(12) United States Patent
Szabo

(10) Patent No.: US 8,167,904 B2
(45) Date of Patent: May 1, 2012

(54) GRIP ARRANGEMENT FOR A MEDICAL INSTRUMENT, AND SUCH MEDICAL INSTRUMENT

(75) Inventor: Zoltan Szabo, San Francisco, CA (US)

(73) Assignee: Karl Storz GmbH & Co. KG (DE)

( * ) Notice: Subject to any disclaimer, the term of this patent is extended or adjusted under 35 U.S.C. 154(b) by 1433 days.

(21) Appl. No.: 10/985,800

(22) Filed: Nov. 10, 2004

(65) Prior Publication Data

US 2005/0119692 A1   Jun. 2, 2005

Related U.S. Application Data

(63) Continuation of application No. PCT/EP03/04289, filed on Apr. 25, 2003.

(30) Foreign Application Priority Data

May 10, 2002 (DE) .................................. 102 22 042

(51) Int. Cl.
*A61B 17/00* (2006.01)
(52) U.S. Cl. ........................................................ 606/205
(58) Field of Classification Search .................... 606/205
See application file for complete search history.

(56) References Cited

U.S. PATENT DOCUMENTS

| 920,092 | A | * | 4/1909 | Slaughter | 30/256 |
|---|---|---|---|---|---|
| 1,116,099 | A | | 11/1914 | Morse | |
| 3,894,336 | A | * | 7/1975 | Desimone | 30/341 |
| 4,268,963 | A | * | 5/1981 | Harrison | 30/262 |
| 4,961,742 | A | | 10/1990 | Torre | 606/147 |
| 5,690,636 | A | | 11/1997 | Wildgoose | 606/88 |
| 6,108,845 | A | | 8/2000 | Hung | 7/128 |
| 6,193,709 | B1 | * | 2/2001 | Miyawaki et al. | 606/1 |
| 6,261,296 | B1 | * | 7/2001 | Aebi et al. | 606/90 |
| 6,533,797 | B1 | * | 3/2003 | Stone et al. | 606/184 |
| 2001/0027312 | A1 | | 10/2001 | Bacher | 606/1 |

FOREIGN PATENT DOCUMENTS

| DE | 42 11 417 A1 | 10/1993 |
|---|---|---|
| DE | 299 02 625 U1 | 8/1999 |
| DE | 198 60 444 A1 | 7/2000 |
| DE | 102 22 042 B3 | 1/2004 |

OTHER PUBLICATIONS

International Search Report, Sep. 9, 2003.
Nadelhalter n. Szabo—Berci.

* cited by examiner

*Primary Examiner* — Gary Jackson
*Assistant Examiner* — L. Bachman
(74) *Attorney, Agent, or Firm* — St. Onge Steward Johnston & Reens LLC

(57) ABSTRACT

A grip arrangement, for a medical instrument having a handle with two rod-shaped grip parts each with a grip surface, has, for each grip, a grip shell which can be secured in a detachable manner on the respective grip part, with in each case a grip surface of the grip parts which is of a larger size and/or of a different shape compared to the grip surface of the grip parts.

22 Claims, 5 Drawing Sheets

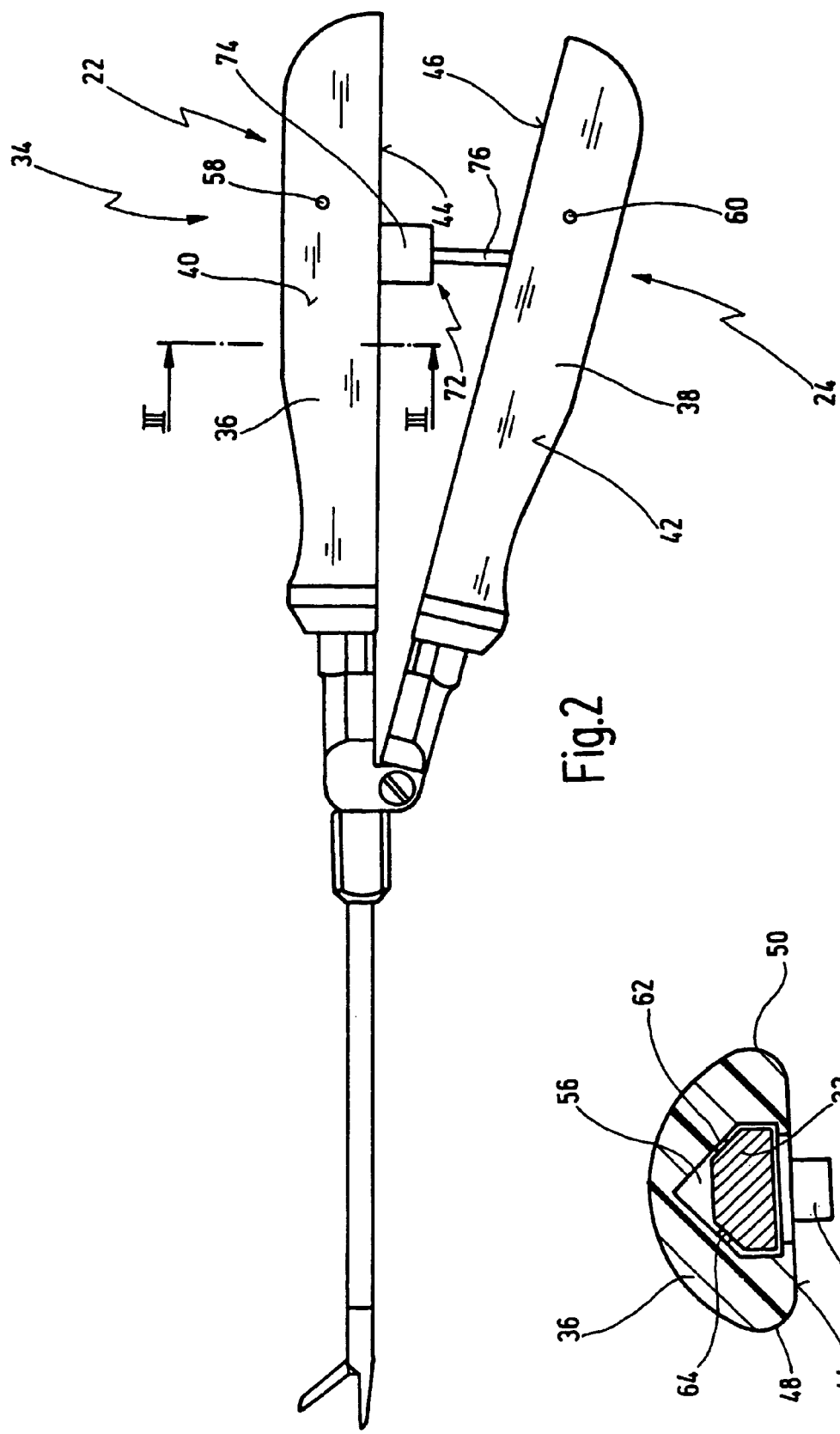
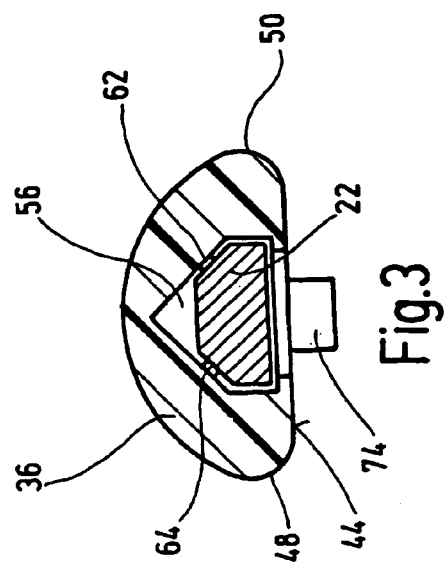
Fig.2
Fig.3

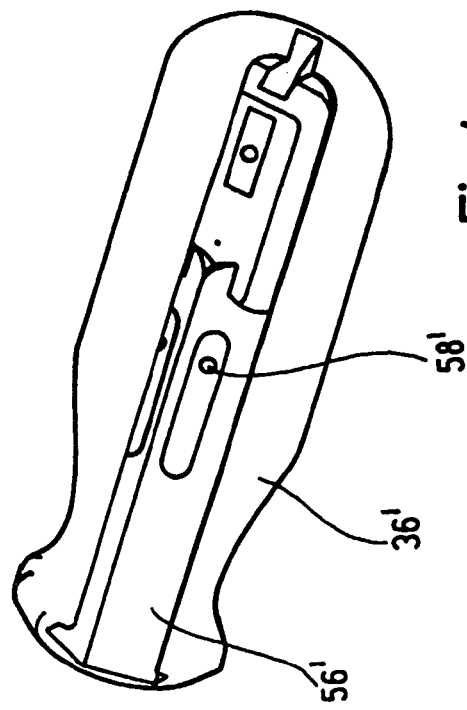
Fig.4b
Fig.4a

GRIP ARRANGEMENT FOR A MEDICAL INSTRUMENT, AND SUCH MEDICAL INSTRUMENT

CROSS REFERENCE TO RELATED APPLICATIONS

The present application is a continuation of pending international patent application PCT/EP 2003/004289 filed on Apr. 25, 2003 which designates the United States, and which claims priority of German patent application 102 22 042.5 filed on May 10, 2002.

BACKGROUND OF THE INVENTION

The invention relates to a grip arrangement for a medical instrument, wherein the instrument has a handle with two substantially rod-shaped grip parts which each have a grip surface.

The invention further relates to an aforementioned medical instrument.

The DE company brochure by the company Karl Storz GmbH & Co. KG, STORZ—Karl Storz Endoskope, volume "Endoskopische Chirurgie" [Endoscopic surgery], 2nd edition 1/94, page NH 3A, discloses a medical instrument in the form of a needle holder whose handle has two rod-shaped grip parts of very slender construction, i.e. having a small cross section in relation to their length. The circumferential surface formed on each grip part and serving as a grip surface is correspondingly small. The grip parts of this known instrument could therefore be regarded as not being optimal from the ergonomic point of view, because the overall grip surface of the grip parts of this instrument is small in relation to the inner surface of the hand of the person using the instrument.

The handle of such an instrument is not only designed so that the instrument can be held in the hand: the grip parts of such an instrument are usually designed to be movable relative to one another so that, by actuating the grip parts, it is possible to operate a tool, for example jaw parts, at the distal end of the instrument. Operating the tool at the distal end of the instrument by means of the grip parts at the proximal end generally requires a firm hold, which is influenced in turn by the ergonomic properties of the grip parts. There is therefore a need to improve the ergonomics of the aforementioned instrument and in particular to adapt them to the particular needs and requirements of the physician.

In addition, medical instruments are known whose handle or handgrip can be removed as a complete unit from the shaft of the instrument, as is described for example in DE 198 60 444 A1. These are complete handles or handgrips which are accordingly also equipped with a force transmission mechanism for actuating the tool at the distal end of the instrument. With removable handles of this kind, it is of course possible to adapt the particular instrument to the particular needs of the operating physician by changing the handgrip for another one, but complete handles of this kind have a complex structure and are expensive if several sets of such handles of different size and shape are to be kept ready.

SUMMARY OF THE INVENTION

It is therefore an object of the invention to make available a grip arrangement for a medical instrument, which grip arrangement makes it possible to improve the ergonomic properties of the instrument at little cost, in particular to adapt it to different requirements of the operating person.

According to an aspect of the invention, this object is achieved by a grip arrangement for a medical instrument of the type mentioned at the outset, which for each grip part has a grip shell which can be secured in a detachable manner on the respective grip part, with in each case a grip surface which is of a larger size and/or of a different shape compared to the grip surface of the grip parts.

With the grip arrangement according to the invention, an already existing instrument can be improved in terms of its ergonomic handling properties without changing the instrument itself, but by fitting on each of the grip parts a grip shell according to the invention, via which grip shell the grip surface of the grip parts is increased in size and/or changed in shape. Holding or gripping of the medical instrument is much improved by means of the grip shells, which define a new grip surface. In addition, a large number of sets of such grip shells of different sizes and/or shapes can be provided for one and the same instrument, as a result of which the handle of the instrument can be adapted to the particular requirements of the operator. In contrast to a removable complete handle, as in the prior art, the grip arrangement according to the invention has the advantage of making it possible to change the handling properties of the instrument at much less cost.

In preferred embodiments, the grip shells are designed so that they can be slid onto the grip parts from the proximal end thereof and/or can be plugged onto the grip parts from the side.

The two variants, which can be provided as alternatives or in combination, represent measures for connecting the grip shells to the respective grip part in an advantageously straightforward way. The slide-on design of the grip shells is suitable in particular for those grip parts which are substantially straight, while the plug-on variant may be better suited for curved grip parts. Plugged on "from the side" is to be understood as meaning that the grip shells, lying side by side with the grip parts, can be mounted on the grip parts transverse to the longitudinal direction.

In a further preferred embodiment, the grip shells are designed as clamp parts to be clamped onto the grip parts.

An advantage of this is that the grip shells simply have to be clamped onto the grip parts in an easy to manipulate manner and in doing so are already at least partially fixed, or even completely fixed, without the need for further fixing operations such as tightening of screws or the like.

In a further preferred embodiment, the grip shells have a depression or recess in which the grip parts are at least partially received when the grip shells are secured.

An advantage of this is that the grip shells can be connected to the grip parts with an especially secure hold, and, as is provided for in a further preferred embodiment, the depressions or recesses can also be designed in such a way that the grip parts are received in them substantially with a form fit. In this way, with a suitable configuration of the depressions or recesses, it is also possible for the grip shells to be mounted on the grip parts in a manner secure against turning and in a predetermined position of rotation easily located with the aid of the form fit.

In this context it is also preferable if the depressions or recesses are designed in such a way that the grip parts are received completely therein, seen in cross section.

An advantage of this is that, when the grip shells are secured on the grip parts, mutually facing sides of the grips shells can form an even surface free of edges. The depressions or recesses can then be designed as completely enclosed bores or openings.

In a further preferred embodiment, when the grip shells are secured on the grip parts, mutually facing sides of the grip shells are each rounded along their edge.

This measure is particularly of advantage if both grip parts can be closed together in contact with one another. The fact that the mutually facing sides of the grip shells are rounded along the edges advantageously means that, when the grip parts are pressed together, it is not possible for skin, in particular the skin of the underside of the hand, to get caught between the grip shells. Another possible way of avoiding skin getting caught is to design the grip shells in such a way that, either with or without a depression/recess, the mutually facing sides of the grip shells are set back from the mutually facing sides of the grip parts.

In a further preferred embodiment, the grip shells each have at least one element for fixing the grip shells on the grip parts in the longitudinal direction and/or transverse direction with respect to the grip parts and/or for securing the grip shells against turning about the longitudinal direction of the grip parts.

By means of these measures, it can be safely ensured that, when the instrument is being used, the grip shells cannot shift or turn relative to the grip parts on which they are secured, nor can they inadvertently lift from the grip parts.

It is preferred if the at least one element is a screw or a catch.

With a screw, for example in the form of a grub screw, which is screwed from outside through the grip shell and for example comes into clamping engagement against the corresponding grip part, it is possible to achieve an especially secure hold of the grip shells particularly against shifting in the longitudinal direction or against turning about the longitudinal direction on the grip parts, while the advantage of a catch as securing element is that arranging the grip shells on the grip parts is made easier because no screw has to be tightened. With a screw, the respective grip shell can also be secured on the grip part with a form fit, for example by screwing the screw into a threaded hole or cylinder hole on the grip part.

In a further preferred embodiment of the at least one element for fixing the grip shells on the grip parts, said at least one element is a bracket which at least partially engages round the corresponding grip part.

Such a bracket secures the grip shells on the grip parts particularly effectively in the transverse direction with respect to the grip parts.

In order to avoid securing the grip shells against turning about the grip parts, the at least one element can advantageously also be formed by the aforementioned recesses or depressions in the grip shells themselves, if the recesses or depressions are designed so that they permit a substantial form fit of the grip parts and if the grip parts are not round in cross section.

In a further preferred embodiment, the grip shells each have a soft and/or roughened grip surface.

With a soft surface, the ergonomic properties of the grip arrangement are advantageously further improved, and a roughened surface advantageously ensures that the grip shells do not slip in the operator's hand.

In a further preferred embodiment, the grip shells have locking means for locking the grip parts in different relative grip positions, these means advantageously permitting stepless locking.

In this embodiment, the grip shells according to the invention not only provide for improved ergonomics of a medical instrument, the grip parts can be given another function which, without the grip shells according to the invention, they previously may not have had. This function entails locking the two grip parts relative to one another in different grip positions. Whereas the grip parts in the known needle holders can already be locked in different locking positions by means of a catch, the grip shells according to the invention are now able to permit stepless locking, for example by two elements which are present on the grip shells and interact with frictional engagement.

As has already been mentioned above, the grip arrangement according to the invention preferably has a large number of sets of grip shells of different sizes and/or shapes, so that an already existing instrument can be adapted to the different requirements of different operators or also to different requirements of the same operator for different applications.

A medical instrument according to the invention is provided with a grip arrangement according to one or more of the aforementioned embodiments.

The grip shells provided according to the invention can preferably be cleaned, in particular autoclaved. This provides the grip arrangement according to the invention with a further advantage over instruments whose handle can be removed as a complete unit from the shaft of the instrument. This is because complete removable handles have, due to their more complicated structure, numerous corners and niches in which dirt and impurities can accumulate and they can be cleaned only with difficulty. By contrast, the structurally very simple grip shells can be designed in one piece and with only a small number of corners and niches, so that dirt and impurities accumulate to a much lesser extent or at least are easier to remove.

Further advantages and features will become apparent from the following description and from the attached drawing.

It will be appreciated that the aforementioned features and those still to be discussed below can be realized not only in the respectively stated combination, but also in other combinations or singly, without departing from the scope of the present invention.

BRIEF DESCRIPTION OF THE DRAWINGS

Illustrative embodiments of the invention are shown in the drawing and are described in more detail below with reference to said drawing, in which:

FIG. 2 shows the instrument from FIG. 1 with a grip arrangement according to the invention secured detachably thereon;

FIG. 3 shows a cross section along the line III-III in FIG. 2 on a slightly enlarged scale;

FIGS. 4a) and 4b) show a further illustrative embodiment of a grip shell of a grip arrangement according to the invention, FIG. 4a) showing the grip shell in a perspective top view and FIG. 4b) showing the grip shell from FIG. 4a) in a perspective view from underneath;

DETAILED DESCRIPTION OF PREFERRED EMBODIMENTS

Figure 1:
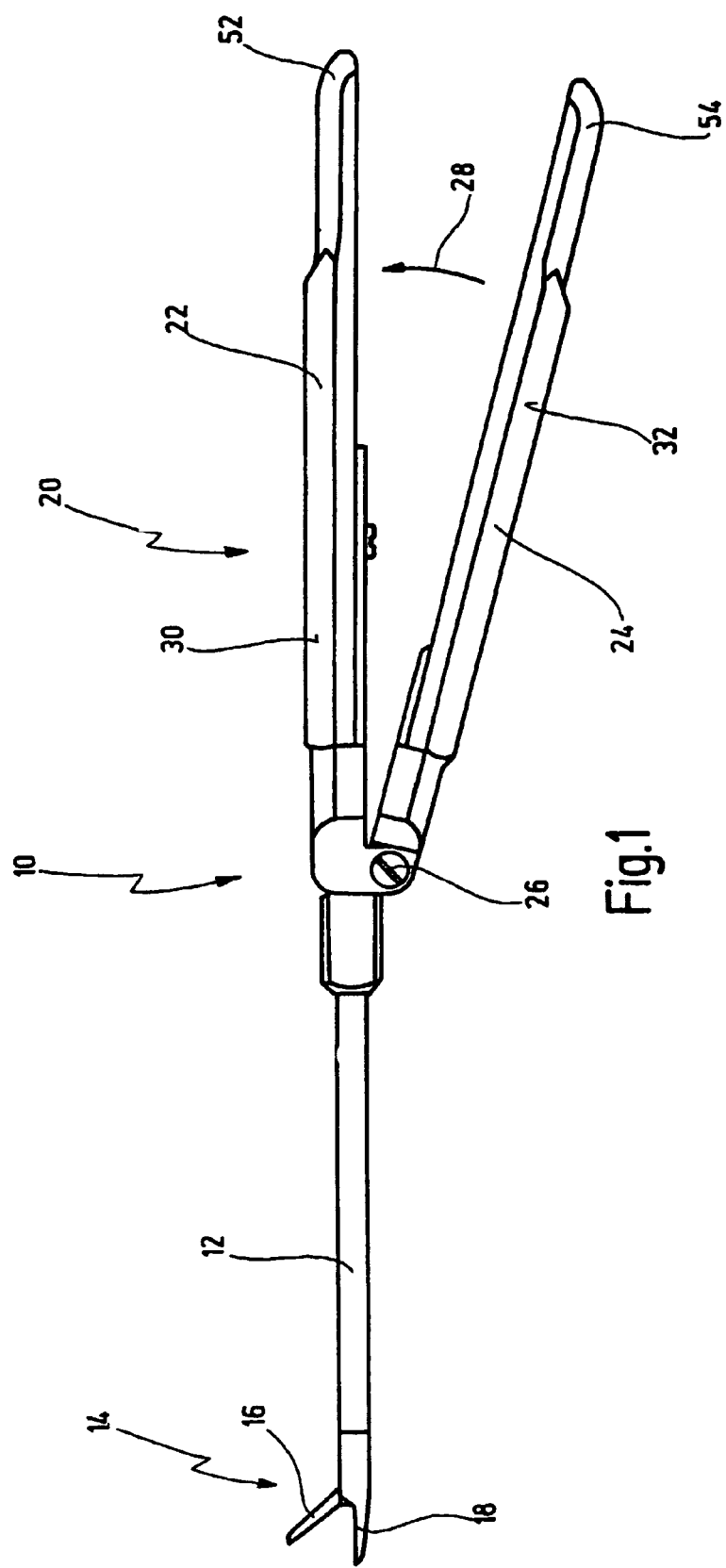
FIG. 1 shows a side view of a medical instrument.

In FIGS. 1 to 3, a medical instrument is shown with general reference number 10. In this illustrative embodiment, the instrument 10 is a needle holder, but in the context of the invention it can also be any other kind of medical instrument, for example a forceps for cutting and/or grasping tissue or generally for dissecting tissue.

The instrument 10 has a shaft 12 at whose distal end a tool 14 is arranged which, in the present illustrative embodiment, has two jaw parts 16 and 18. The jaw part 16 is movable, whereas the jaw part 18 is immovable. When the jaw parts 16 and 18 are closed, a needle (not shown) can be held between said jaw parts 16 and 18.

At the proximal end of the shaft 12, the instrument has a handle 20 with a first grip part 22 and a second grip part 24. The first grip part 22 is immovable, whereas the second grip part 24 can be pivoted relative to the first grip part 22 about a pivot axis 26. By pivoting the second grip part 24 in the direction of an arrow 28, the movable jaw part 16 is closed against the immovable jaw part 18. The force transmission from the movable grip part 24 to the movable jaw part 16 is effected via a force transmission mechanism (not shown in detail) which comprises a push rod, as is customary in instruments of this kind.

The grip parts 22 and 24 are of rod-shaped design and, in the present illustrative embodiment, they follow a rectilinear course. The grip parts 22 and 24, seen in cross section (cf. FIGS. 1 and 3), are of slender design in relation to their length. Accordingly, grip surfaces 30 and 32 of the grip parts 22 and 24 are narrow and not optimally adapted to the palm of the operators hand. The grip surfaces 30 and 32 are formed by the top surfaces of the grip parts 22 and 24, specifically those surfaces of the grip parts 22 and 24 facing away from one another.

In order to increase the size or possibly change the shape of the grip surfaces 30 and 32 of the grip parts 22 and 24, and thus make them more ergonomic as a whole, a grip arrangement 34 according to FIG. 2 is provided which has a first grip shell 36 and a second grip shell 38.

The grip shells 36 and 38 are secured detachably on the respective grip part 22 and 24 in the area of the grip surfaces 30, 32 thereof.

The first grip shell 36 has a grip surface 40, and the second grip shell 38 has a second grip surface 42 which, as will be clear from a comparison of FIGS. 1 and 2 and in particular from FIG. 3, is larger compared to the grip surfaces 30 and 32 of the grip parts 22 and 24.

The grip shells 36 and 38 are designed, in terms of their size and/or shape, so that they are adapted to the particular needs of the operator.

When the grip shells 36 and 38 are secured, mutually facing sides 44 and 46 of the grip shells 36 and 38 are each rounded along their edge, as is shown in FIG. 3 for the grip shell 36, which has rounded areas 48 and 50. The rounded areas 48 and 50 mean that the skin of the hand holding the instrument 10 does not get caught between the grip shells 36 and 38 when the grip parts 22 and 24 are closed or pressed together.

In the illustrative embodiment shown, the grip shells 36 and 38 are designed so that they can be slid onto the grip parts 22 and 24, respectively, from the proximal end 52 and 54, respectively.

The grip shells 36 and 38 each have a depression or recess 56 which extends in the longitudinal direction of the grip shells 36 and 38 and is designed in the form of a groove, FIG. 3 showing the recess or depression 56 for the grip shell 36 in cross section. On this point, reference is also made to FIGS. 4b) and 5a) which show grip shells 36' and 38', respectively, which have a depression or recess 56' designed as a groove and corresponding to the depression 56 of the grip shells 36 and 38.

When the grip shells 36 and 38 are secured, the grip parts 22 and 24 are received at least partially in the depression or recess 56; in the illustrative embodiment shown in cross section in FIGS. 1 to 3 they are received completely therein.

The grip shells 36 and 38 each have at least one element 58 and 60 for fixing the grip shells 36 and 38 on the grip parts 22 and 24.

Figure 5A:
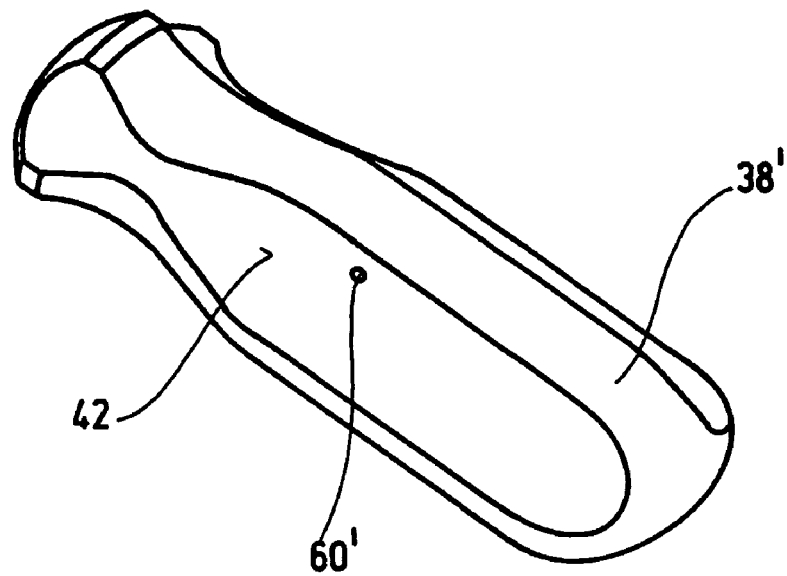
FIGS. 5a) and 5b) show views, corresponding to FIGS. 4a) and 4b), of a further illustrative embodiment of a grip shell.

The elements 58 and 60 are, for example, designed as screws, for example grub screws 62, 64, which can be screwed in through corresponding openings in the grip shells 36 and 38, respectively, and can be brought into clamping engagement with the grip parts 22 and 24. The grip parts 22 and 24 could, however, also be provided with threaded holes or cylinder holes into which the screws 62, 64 can be turned or can engage. The elements 58, 60 thus apply the grip shells 36, 38 to the grip parts 22, 24 fixedly in the longitudinal direction thereof. Instead of or in addition to the screw connection, however, the grip shells 36 and 38 can also be fixed on the grip parts 22 and 24 by, for example, a catch 65 (cf. FIG. 5a).

Moreover, in the illustrative embodiment according to FIGS. 1 to 3, the grip shells 36 and 38 are also fixed by virtue of the fact that the grip parts 22 and 24 are bordered on all sides by the respective depression or recess 56 of the grip shell 36, 38, as is evident from FIG. 3. In this way, the grip shells 36 and 38 can also be fixed thereon in the transverse direction with respect to the grip parts 22 and 24.

The grip parts 22 and 24 in the illustrative embodiment in FIGS. 1 to 3 have a cross section which is not round, but instead polygonal, so that the substantial form fit of the grip parts 22 and 24 in the grip shells 36 and 38, respectively, also secures the grip shells 36 and 38 against turning about the longitudinal direction of the grip parts 22 and 24, respectively.

Figure 6:
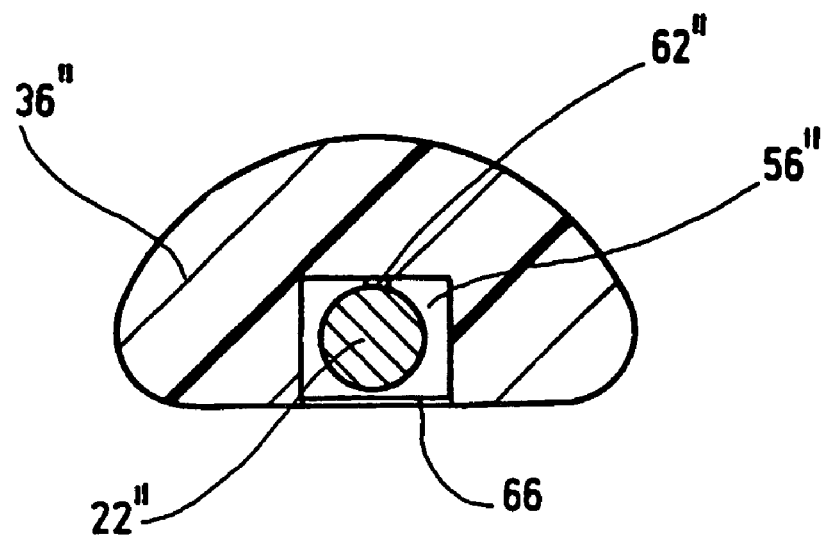
FIGS. 6 and 7 show two cross-sectional views, corresponding to FIG. 3, of further illustrative embodiments of grip arrangements.

In the case of a cylindrical design of a grip part 22", however, screws can also provide this security against turning, as is shown for example in FIG. 6 for a grip part 22" of round cross section and a grip shell 36" with screw 62", where the grip part 22" is received, not with a form fit, in the recess or depression 56" of the grip shell 36".

In the illustrative embodiment shown in FIG. 6, in order also to fix the grip shell 36" in the transverse direction, that is to say transversely with respect to the longitudinal direction of the grip part 22", in particular in the direction of actuation of the grip part 22", the grip shell 36" has at least one bracket 66 which engages at least partially round the grip part 22", or engages completely round it as in FIG. 6. A plurality of such brackets 66 can be provided along the length of the grip shell 36", or the depression or recess 56" can be designed as a bore or recess closed on all sides in cross section.

Figure 7:
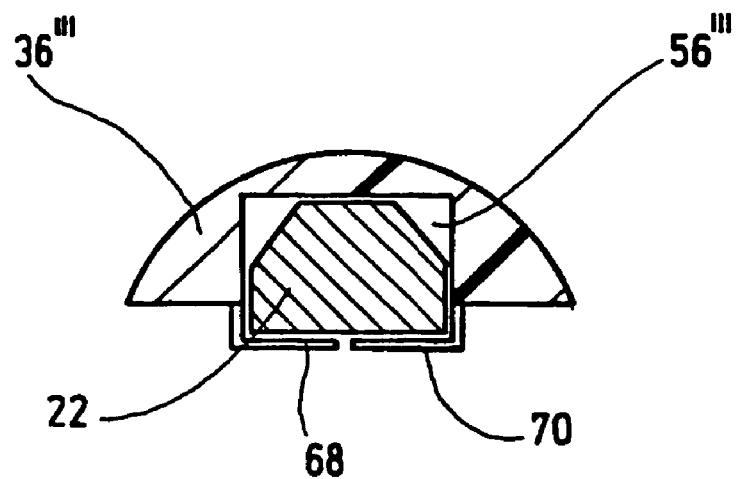

In FIG. 7, an illustrative embodiment is shown in which a grip shell 36''' is designed as a clamp part to be clamped onto the grip part 22. In this configuration, the shell 36''' can be slid onto the grip part 22 in the longitudinal direction thereof. In the illustrative embodiment shown in FIG. 7, the grip shell 36''' also has a depression or recess 56''' in which the grip part 22 is received only partially. To clamp the grip shell 36''' on the grip part 22, the grip shell 36''' has brackets 68 and 70 which are suitably elastic and act as clamps. The brackets 68 and 70 at the same time serve as elements for fixing the grip shell 36''' in the transverse direction with respect to the grip part 22, i.e. transversely with respect to the longitudinal direction, in particular in the direction of actuation of the grip part 22. With the brackets 68 and 70 suitably made as elastic elements, and with a suitable geometry of the brackets 68 and 70, the grip shell 36''' could also be plugged onto the grip part 22, transversely to the longitudinal direction thereof, in the manner of a clip, in which case the brackets 68 and 70 spread apart during fitting and then close in around the grip part 22.

With reference again to FIGS. 2 and 3, the grip shells 36 and 38 have locking means 72 for locking the grip parts 22 and 24 in different relative gripping positions with respect to one another. The locking means 72 have, for example, a sleeve 74 connected to the grip shell 36, and a pin 76 which is connected to the grip shell 38 and engages with friction in the sleeve 74 and permits stepless locking of the grip parts 22 and 24 on one another.

Figure 5B:
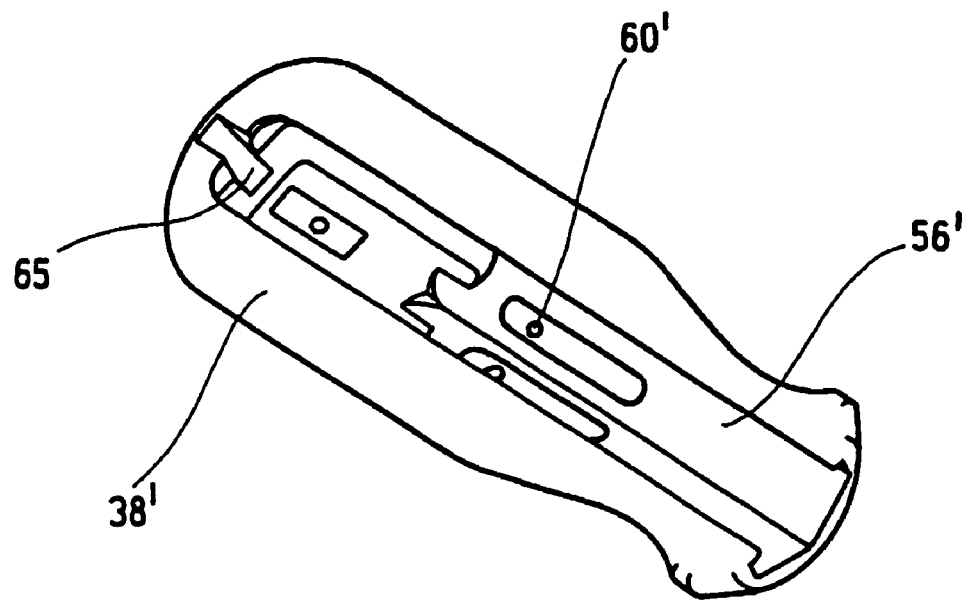

The grip parts 36' and 38' shown in FIGS. 4 and 5 can likewise be secured on the grip parts 22 and 24 of the instrument 10, the grip part 36' having a grip surface 40' which is adapted in particular to the palm in the area of the thumb and preferably has a thumb indent 78, while the grip shell 38' has a grip surface 42' adapted to the lower area of the palm.

The grip surfaces 40 and 42 of the grip shells 36 and 38 are preferably soft and/or roughened. The grip shells 36 and 38 can also be autoclaved.

It will be appreciated that a number of sets of grip shells 36 and 38 of different sizes and/or different shapes can be kept in stock for the instrument 10, so as to be able to adapt the handle 20 of the instrument 10 to the particular needs and requirements of the operator.

What is claimed is:

1. A grip arrangement for a medical instrument, which instrument has a handle with two substantially rod-shaped grip parts each with a grip surface, said grip arrangement comprising for each said grip part a rod-shaped grip shell which can be secured in a detachable manner on said respective grip part so that said respective grip shell is arranged on said respective grip surface of said respective grip part, each said grip shell having a grip surface which is of a larger size compared to said grip surface of said grip parts.

2. The grip arrangement of claim 1, wherein said grip surface of each said grip shell is of a different shape compared to said grip surface of said grip parts.

3. The grip arrangement of claim 1, wherein said grip shells are designed so that they can be slid onto said grip parts from a proximal end of said grip parts.

4. The grip arrangement of claim 1, wherein said grip shells are designed so that they can be plugged onto said grip parts from a side of said grip parts.

5. The grip arrangement of claim 1, wherein said grip shells are designed as clamp parts to be clamped onto said grip parts.

6. The grip arrangement of claim 1, wherein said grip shells have a recess in which said grip parts are at least partially received when said grip shells are secured to said grip parts.

7. The grip arrangement of claim 6, wherein said recesses are designed so that said grip parts are received completely in said recesses, seen in cross section.

8. The grip arrangement of claim 6, wherein said recesses are designed to receive said grip parts substantially with a form fit.

9. The grip arrangement of claim 1, wherein mutually facing sides of said grip shells, when secured on said grip parts, are each rounded along an edge of said sides.

10. The grip arrangement of claim 1, wherein said grip shells each have at least one element for fixing said grip shells on said grip parts in a longitudinal direction with respect to said grip parts.

11. The grip arrangement of claim 1, wherein said grip shells each have at least one element for fixing said grip shells on said grip parts in a transverse direction with respect to said grip parts.

12. The grip arrangement of claim 1, wherein said grip shells each have at least one element for securing said grip shells against turning about a longitudinal direction of said grip parts.

13. The grip arrangement of claim 1, wherein said grip shells each have a soft surface.

14. The grip arrangement of claim 1, wherein said grip shells each have a roughened grip surface.

15. The grip arrangement of claim 1, wherein said grip shells have locking means for locking said grip parts in different relative grip positions.

16. The grip arrangement of claim 15, wherein said locking means permit stepless locking of said grip parts in different relative grip positions.

17. The grip arrangement of claim 1, wherein said arrangement comprises a large number of sets of grip shells of at least one of different sizes and different shapes.

18. The grip arrangement of claim 1, wherein said grip shells can be autoclaved.

19. A medical instrument, comprising a handle with two substantially rod-shaped grip parts each with a grip surface which allows operation of the medical instrument, wherein for each said grip part at least one rod-shaped grip shell is provided which can be secured in a detachable manner on said respective grip parts, said at least one grip shell having a grip surface which is of a larger size compared to said grip surface of said grip parts.

20. The medical instrument of claim 19, wherein said grip surface of said at least one grip shell is of a different shape compared to said grip surface of said grip parts.

21. A grip arrangement for a medical instrument, which instrument has a handle with two substantially rod-shaped grip parts each with a grip surface which allows operation of the medical instrument, said grip arrangement comprising for each said grip part a rod-shaped grip shell which can be secured in a detachable manner on said respective grip part so that said respective grip shell is arranged on said respective grip surface of said respective grip part, each said grip shell having a grip surface which is of a larger size compared to said grip surface of said grip parts.

22. A grip arrangement for a medical instrument, which instrument has a handle with two substantially rod-shaped grip parts each with a grip surface, said grip arrangement comprising for each said grip part a rod-shaped grip shell which can be secured in a detachable manner on said respective grip part so that said respective grip shell is arranged on said respective grip surface of said respective grip part, each said grip shell having a grip surface which is of a larger size compared to said grip surface of said grip parts;
  wherein said grip shells have locking means that permit stepless locking of said grip parts in different relative grip positions.

\* \* \* \* \*